United States Patent [19]

Hansenne et al.

[11] Patent Number: 5,993,788
[45] Date of Patent: Nov. 30, 1999

[54] STABLE PHOTOPROTECTIVE COMPOSITIONS COMPRISING DIBENZOYLMETHANE COMPOUNDS/ POLYSACCHARIDE

[75] Inventors: Isabelle Hansenne, Paris; Karine De Chabannes, Orléans, both of France

[73] Assignee: Societe L'Oreal S.A., Paris, France

[21] Appl. No.: 08/834,981

[22] Filed: Apr. 7, 1997

[30] Foreign Application Priority Data

Apr. 5, 1996 [FR] France .................................. 96 04361

[51] Int. Cl.[6] .................................................... A61K 7/42
[52] U.S. Cl. ............................................................ 424/59
[58] Field of Search .................................................. 424/59

[56] References Cited

U.S. PATENT DOCUMENTS 4,387,089  6/1983  De Polo .................................... 424/59
5,618,522  4/1997  Kaleta et al. ............................. 424/60

FOREIGN PATENT DOCUMENTS 2440933  6/1980  France .

*Primary Examiner*—S. Mark Clardy
*Assistant Examiner*—Michael A. Williamson
*Attorney, Agent, or Firm*—Burns, Doane, Swecker & Mathis, L.L.P.

[57] ABSTRACT

Topically applicable, stable, photoprotective cosmetic/dermatological compositions, well suited for improved photoprotection of human skin and/or hair against the damaging effects of UV irradiation, particularly solar radiation, comprise (a) an effective photoprotecting amount of at least one dibenzoylmethane compound and (b) an effective photostabilizing amount of at least one polysaccharide alkyl ether.

27 Claims, No Drawings

STABLE PHOTOPROTECTIVE COMPOSITIONS COMPRISING DIBENZOYLMETHANE COMPOUNDS/ POLYSACCHARIDE

BACKGROUND OF THE INVENTION

1. Technical Field of the Invention

The present invention relates to novel topically applicable cosmetic and/or dermatological compositions well suited for the photoprotection of the skin and/or the hair against ultraviolet radiation (referred to hereinbelow more simply as "screening" or "sunscreen" compositions) and to a general technique for the photostabilization of specific UV-A-active sunscreens by means of particular polysaccharide alkyl ethers.

More especially, this invention relates to UV-photostable screening compositions which comprise, in a topically applicable, cosmetically and/or dermatologically acceptable vehicle, diluent or carrier, at least one dibenzoylmethane compound active as a UV-A organic sunscreen, together with a particular polysaccharide alkyl ether as a photostabilizing agent therefor, and to a corresponding process for the stabilization of such at least one dibenzoylmethane compound by means of said polysaccharide alkyl ether.

2. Description of the Prior Art

It is known that light radiation of wavelengths of from 280 nm to 400 nm promotes tanning of the human epidermis, and that light rays of wavelengths of from 280 nm to 320 nm, i.e., UV-B irradiation, cause skin burns and erythema which may be harmful to the natural development of the tan; hence, such UV-B radiation should be screened from the skin.

It is also known to this art that UV-A radiation, of wavelengths of from 320 nm to 400 nm, which causes tanning of the skin, also adversely affects it, especially in the case of sensitive skin or of skin which is continually exposed to solar radiation. UV-A irradiation causes, in particular, a loss in the elasticity of the skin and the appearance of wrinkles, promoting premature skin aging. Such irradiation promotes triggering of the erythemal reaction or amplifies this reaction in certain individuals and may even be the cause of phototoxic or photoallergic reactions. Thus, it is desirable to also screen out UV-A radiation.

In this respect, one particularly advantageous class of UV-A screening agents currently in use comprises dibenzoylmethane derivatives, and in particular 4-(tert-butyl)-4'-methoxydibenzoylmethane, which exhibit a high intrinsic power of absorption. These dibenzoylmethane derivatives, which are compounds that are well known per se as UV-A-active screening agents, are described in FR-A-2,326,405 and FR-A-2,440,933, as well as in EP-A-0,114,607; 4-(tert-butyl)-4'-methoxydibenzoylmethane is moreover currently commercially available under the trademark "Parsol 1789" from Givaudan.

Unfortunately, these dibenzoylmethane derivatives are compounds which are relatively sensitive to ultraviolet radiation (especially UV-A), namely, more precisely, they have an unfortunate tendency to degrade relatively rapidly under the action of ultraviolet radiation. Hence, this substantial lack of photochemical stability of dibenzoylmethane derivatives towards ultraviolet radiation, to which they are by nature intended to be subjected, does not make it possible to guarantee constant protection during prolonged exposure to the sun, such that the user must make repeated applications at close and regular time intervals in order to obtain effective protection of the skin against UV irradiation, which obviously is a disadvantage.

To date, the photostabilization of dibenzoylmethane derivatives with respect to UV radiation remains a problem which has not yet been solved entirely satisfactorily.

SUMMARY OF THE INVENTION

It has now surprisingly and unexpectedly been found that by combining an effective amount of at least one specific polysaccharide alkyl ether with the aforesaid dibenzoylmethane derivatives, the photochemical stability (or photostability) of said dibenzoylmethane derivatives is substantially and markedly improved.

Briefly, the present invention thus features novel compositions well suited for protecting the skin and/or the hair against the deleterious effects of ultraviolet radiation, said compositions comprising, in particular in a topically applicable, cosmetically acceptable vehicle, diluent or carrier, at least one dibenzoylmethane compound and at least one polysaccharide alkyl ether which comprises structural units containing at least two different monosaccharide rings, each unit containing at least one hydroxyl group substituted with a saturated hydrocarbon alkyl chain.

The compositions in accordance with the invention present the advantage of being particularly photostable, even after prolonged exposure to UV-A and UV-B radiation. This radiation may be of natural origin (sun) or artificial origin (UV lamp).

The present invention also features a technique for the stabilization of dibenzoylmethane derivatives with respect to UV radiation, comprising intimately admixing said dibenzoylmethane derivatives with an effective photostabilizing amount of at least one polysaccharide alkyl ether which comprises structural units containing at least two different monosaccharide rings, each unit containing at least one hydroxyl group substituted with a saturated hydrocarbon alkyl chain.

Too, the present invention features a cosmetic treatment or regimen for protecting human skin and/or hair against the damaging effects of ultraviolet radiation, comprising topically applying thereto an effective photoprotective amount of a photostable composition as described above.

DETAILED DESCRIPTION OF BEST MODE AND SPECIFIC/PREFERRED EMBODIMENTS OF THE INVENTION

More particularly according to the present invention, the dibenzoylmethane derivatives photostabilized thereby are known compounds which are described, in particular, in FR-A-2,326,405, FR-A-2,440,933 and EP-A-0,114,607.

According to the present invention, one or more dibenzoylmethane derivatives may of course be used.

Particularly exemplary of such dibenzoylmethane derivatives are:

2-Methyldibenzoylmethane,
4-Methyldibenzoylmethane,
4-Isopropyldibenzoylmethane,
4-Tert-butyldibenzoylmethane,
2,4-Dimethyldibenzoylmethane,
2,5-Dimethyldibenzoylmethane,
4,4'-Diisopropyldibenzoylmethane,
4-Tert-butyl-4'-methoxydibenzoylmethane,
2-Methyl-5-isopropyl-4'-methoxydibenzoylmethane,
2-Methyl-5-tert-butyl-4'-methoxydibenzoylmethane,
2,4-Dimethyl-4'-methoxydibenzoylmethane, and 2,6-Dimethyl-4-tert-butyl-4'-methoxydibenzoylmethane.

Among the aforesaid dibenzoylmethane derivatives, it is most particularly preferred to employ 4-(tert-butyl)-4'-methoxydibenzoylmethane, especially that commercially available under the trademark "Parsol 1789" from Givaudan, this screening agent having the following structural formula:

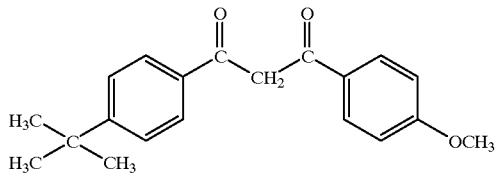

Another preferred dibenzoylmethane derivative according to the present invention is 4-isopropyldibenzoylmethane, this screening agent being commercially available under the trademark "Eusolex 8020" from Merck, and having the following structural formula:

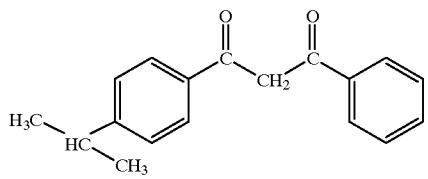

The dibenzoylmethane derivative or derivatives are advantageously formulated into the compositions in accordance with the invention, or into compositions sought to be stabilized therewith, at concentrations generally ranging from 0.01% to 10% by weight, and preferably at concentrations ranging from 0.3% to 5% by weight, relative to the total weight of the composition.

In one specific embodiment of the invention, the polysaccharide alkyl ether has a molecular weight greater than 100,000 and preferably greater than 200,000. Each structural unit may contain from one to six and preferably from two to four hydroxyl groups substituted with a saturated hydrocarbon alkyl chain.

By "saturated hydrocarbon alkyl chain" is intended a chain having from 1 to 24, preferably from 1 to 10 and more preferably from 1 to 5, carbon atoms. Particularly exemplary alkyl moieties include methyl, ethyl, n-propyl, isopropyl, n-butyl, isobutyl, tert-butyl and n-pentyl radicals.

The monosaccharide rings members are advantageously selected from among mannose, galactose, glucose, furanose, rhamnose and arabinose.

In a preferred embodiment of the invention, the polysaccharide alkyl ether is an alkyl ether of a gum and, more particularly, of an overall nonionic gum, namely, one with virtually no ionic groups. Suitable gums which are exemplary are guar gum, whose structural unit comprises a galactose and a mannose moiety, carob gum, whose structural unit comprises a galactose and a mannose moiety, karaya gum, which is a complex mixture of rhamnose, galactose and galacturonic acid, and gum tragacanth, which is a complex mixture of arabinose, galactose and galacturonic acid.

In a particularly preferred embodiment of the invention, the polysaccharide alkyl ether is a guar gum derivative, and more especially ethyl guar having a degree of substitution of about 2 to 3, in particular 2.5, as described in RD-95378007 (October 1995).

By the expression "effective amount of polysaccharide alkyl ether" according to the invention is intended an amount which is sufficient to provide an appreciable and significant improvement in the photostability of the dibenzoylmethane derivative or derivatives contained in the composition. The minimum amount of stabilizer to be used, which may vary according to the nature of the cosmetically acceptable vehicle selected for the composition, may be determined without difficulty by means of a standard test for measuring photostability, such as that indicated in the examples below.

The compositions according to the invention may contain, for example, an amount of polysaccharide alkyl ether ranging from 0.5% to 20%, and preferably from 2% to 10%, of the total weight of the composition.

The photostable screening cosmetic compositions according to the invention may of course also contain, other than the dibenzoylmethane derivatives, one or more hydrophilic or lipophilic UVA- and/or UVB-active complementary sunscreens. The presence of complementary screening agents which are active in the UV-B range (wavelengths ranging from approximately 280 nm to 320 nm) thus permits formulating final compositions suitable for screening out all UV irradiation.

The compositions of the invention may also comprise standard cosmetic and/or dermatological adjuvants and additives selected, in particular, from among fatty substances, organic solvents, ionic or nonionic thickeners, softeners, antioxidants, opacifying agents, stabilizers, emollients, silicones, a-hydroxy acids, anti-foaming agents, moisturizers, vitamins, fragrances, preservatives, surfactants, fillers, pigments and colorants (inorganic or organic), sequestering agents, polymers, propellants, basifying or acidifying agents, dyes, or any other ingredient typically employed in cosmetics, in particular for the manufacture of screening compositions. Naturally, all such additional ingredients which may be introduced into the compositions of the invention must be such that they do not substantially disrupt or adversely affect the photostabilization activity elicited by the polysaccharide alkyl ether on the dibenzoylmethane derivatives.

The fatty substances may comprise an oil or a wax or mixtures thereof; they also comprise fatty acids, fatty alcohols and fatty acid esters. The oils may be selected from among animal, plant, mineral or synthetic oils and, in particular, from among liquid petrolatum, liquid paraffin, volatile or non-volatile silicone oils, isoparaffins, poly-α-olefins, fluoro oils and perfluoro oils. Similarly, the waxes may be selected from among animal, fossil, plant, mineral or synthetic waxes that are per se known to this art.

Exemplary organic solvents include the lower alcohols and polyols having less than 8 carbon atoms.

The thickeners other than the polysaccharide alkyl ether according to the invention are advantageously selected from among crosslinked polyacrylic acids and modified or non-modified celluloses, such as methylhydroxyethylcellulose, hydroxypropylmethylcellulose and hydroxyethylcellulose.

The compositions of the invention may be formulated via any technique well known to this art.

These subject compositions may, in particular, be formulated as an oil or a simple or complex emulsion (O/W, W/O, O/W/O or W/O/W).

Preferably, the compositions of the invention are formulated as oils.

When the composition is an emulsion, the aqueous phase thereof may comprise a nonionic vesicle dispersion prepared according to known processes (Bangham, Standish and Watkins, *J. Mol. Biol.*, 13, 238 (1965), FR-2,315,991 and FR-2,416,008.

The photostable cosmetic compositions of the invention are well suited for protecting human skin or hair against ultraviolet radiation, as screening compositions, or as makeup products.

When the cosmetic compositions according to the invention are used for protecting human skin against UV irradiation or as screening compositions, they may be formulated as a suspension or dispersion in solvents or fatty substances, as a nonionic vesicle dispersion, or alternatively, as an emulsion, preferably of oil-in-water type, such as a cream, lotion or a milk, or as an ointment, a gel, a solid stick, a stick, an aerosol foam or a spray.

When the cosmetic compositions according to the invention are used for protecting the hair, they are advantageously formulated as a shampoo, a lotion, a gel, an emulsion, a nonionic vesicle dispersion or a lacquer for the hair and may constitute, for example, a rinse composition to be applied before or after shampooing, before or after dyeing or bleaching, before, during or after permanent-waving or straightening of the hair, as a styling or treating lotion or gel, as a blow-drying or hair-setting lotion or gel, or as a composition for permanent-waving, straightening, dyeing or bleaching the hair.

When the subject compositions comprise a makeup product for the eyelashes, the eyebrows or the skin, such as a skin treatment cream, a foundation, a lipstick or lipcolor, an eye shadow, a blusher, a mascara or an eyeliner, they may be in anhydrous or aqueous, solid or pasty form, for example powders, oil-in-water or water-in-oil emulsions, nonionic vesicle dispersions or suspensions.

In order to further illustrate the present invention and the advantages thereof, the following specific examples are given, it being understood that same are intended only as illustrative and in nowise limitative.

EXAMPLE 1

The following specific compositions were formulated (the amounts are expressed as a percentage by weight relative to the total weight of the composition):

(a) 4-tert-butyl-4'-methoxydibenzoylmethane (Parsol 1789) 2%
(b) (C12/C15) alkyl benzoate, marketed under the trademark "Finsolv TN" by Stéarineries Dubois 4%
(c) ethyl guar having a degree of substitution of about 2.5 x%
(d) isopropyl palmitate q.s. 100%

The various compositions are set forth in Table I below, according to the value of x:

TABLE I

| Composition | Ethyl guar (x%) |
| --- | --- |
| A (comparative) | 0 |
| B (invention) | 4 |
| C (invention) | 7 |

The compositions were prepared by simple mixing of the constituents heated to about 60° C.

For each of these compositions, the percentage of residual 4-tert-butyl-4'-methoxydibenzoylmethane after irradiation over the entire UV spectrum (280–400 nm) was determined according to the following procedure: for each composition, four control samples and four test samples were prepared. 16 mg of composition, which was spread over a surface of 2×4 cm$^2$, were placed on frosted PMMA (polymethyl methacrylate) plates, which had been rinsed beforehand with water and then dried.

The plates were then all left to stand for one-half hour in darkness. The plates were then irradiated over the entire UV spectrum (Heraeus Suntest CPS) for 30 minutes, while the control plates were maintained in darkness during the period of irradiation of the other plates.

The samples were then assayed in the following manner: the screening agents were extracted by immersing each plate in 50 g of isopropanol in order to dissolve the screening agents. The plates and the solvent containing the screening agents were then treated with ultrasound for 5 minutes in order to ensure efficient stirring. The concentration of residual 4-tert-butyl-4'-methoxydibenzoylmethane was measured by spectrophotometry at the absorption maximum of the 4-tert-butyl-4'-methoxydibenzoylmethane (355 nm).

The results, as a percentage of the concentration of residual 4-tert-butyl-4'-methoxydibenzoylmethane relative to the initial concentration of 4-tert-butyl-4'-methoxydibenzoylmethane, are reported in Table II below:

TABLE II

| Composition | Residual Parsol 1789 |
| --- | --- |
| A (comparative) | 67% |
| B (invention) | 80.5% |
| C (invention) | 81% |

These results clearly evidence that the presence of a polysaccharide alkyl ether according to the invention in a composition containing 4-tert-butyl-4'-methoxydibenzoyl methane (Parsol 1789) significantly increased the stability of the latter in the subject composition.

EXAMPLE 2

A specific example of a sunscreen oil according to the invention is set forth below. The amounts are expressed by weight relative to the total weight of the composition.

| Sunscreen oil: | |
| --- | --- |
| (a) 4-tert-butyl-4'-methoxydibenzoylmethane (Parsol 1789) | 1.25% |
| (b) 2-ethylhexyl α-cyano-β,β'-diphenylacrylate, marketed under the trademark "Uvinul N 539" by BASF | 3.75% |
| (c) ethyl guar having a degree of substitution of about 2.5 | 4% |
| (d) isononyl isononanoate from Stéarineries Dubois | q.s. 100% |
| (e) dyes | q.s. |
| (f) fragrance | q.s. |

This composition was prepared by simple mixing of the constituents heated to about 60° C.

This sunscreen oil was particularly photostable and ensured protection over the entire range of UV radiation.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A stable photoprotective cosmetic/dermatological composition, comprising (a) an effective amount of at least one dibenzoylmethane compound and (b) an effective photostabilizing amount of at least one polysaccharide alkyl ether wherein said at least one polysaccharide alkyl ether comprises structural units containing at least two different monosaccharide ring members, and each unit comprises at least one alkyl ether substituent.

2. The photoprotective cosmetic/dermatological composition as defined by claim 1, formulated into a topically applicable, cosmetically/dermatologically acceptable vehicle, diluent or carrier therefor.

3. The photoprotective cosmetic/dermatological composition as defined by claim 1, each said alkyl ether substituent having from 1 to 24 carbon atoms.

4. The photoprotective cosmetic/dermatological composition as defined by claim 3, each said alkyl ether substituent having from 1 to 5 carbon atoms.

5. The photoprotective cosmetic/dermatological composition as defined by claim 4, each said alkyl ether substituent comprising a methyl, ethyl, n-propyl, isopropyl, n-butyl, isobutyl or tert-butyl radical.

6. The photoprotective cosmetic/dermatological composition as defined by claim 1, each said monosaccharide ring member comprising mannose, galactose, glucose, furanose, rhamnose or arabinose.

7. The photoprotective cosmetic/dermatological composition as defined by claim 1, said at least one polysaccharide alkyl ether comprising an alkyl ether of guar gum, carob gum, karaya gum, gum tragacanth, or mixture thereof.

8. The photoprotective cosmetic/dermatological composition as defined by claim 7, said at least one polysaccharide alkyl ether comprising an alkyl ether of a guar gum, the degree of substitution of which ranging from 2 to 3.

9. The photoprotective cosmetic/dermatological composition as defined by claim 1, said at least one polysaccharide alkyl ether having a molecular weight greater than 200,000.

10. The photoprotective cosmetic/dermatological composition as defined by claim 1, said at least one polysaccharide alkyl ether comprising from 0.5% to 20% by weight thereof.

11. The photoprotective cosmetic/dermatological composition as defined by claim 10, said at least one polysaccharide alkyl ether comprising from 2% to 10% by weight thereof.

12. The photoprotective cosmetic/dermatological composition as defined by claim 1, said at least one dibenzoylmethane compound comprising 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, or 2,6-dimethyl-4-tert-butyl-4'-methoxydibenzoylmethane.

13. The photoprotective cosmetic/dermatological composition as defined by claim 12, said at least one dibenzoylmethane compound comprising 4-(tert-butyl)-4'-methoxydibenzoylmethane.

14. The photoprotective cosmetic/dermatological composition as defined by claim 12, said at least one dibenzoylmethane compound comprising 4-isopropyldibenzoylmethane.

15. The photoprotective cosmetic/dermatological composition as defined by claim 1, said at least one dibenzoylmethane compound comprising from 0.01% to 10% by weight thereof.

16. The photoprotective cosmetic/dermatological composition as defined by claim 15, said at least one dibenzoylmethane compound comprising from 0.3% to 5% by weight thereof.

17. The photoprotective cosmetic/dermatological composition as defined by claim 1, further comprising at least one cosmetically/dermatologically acceptable adjuvant or additive.

18. The photoprotective cosmetic/dermatological composition as defined by claim 17, said at least one adjuvant or additive comprising a fat, organic solvent, ionic or nonionic thickening agent, softener, antioxidant, opacifying agent, stabilizing agent, emollient, silicone, $\alpha$-hydroxy acid, antifoaming agent, moisturizer, vitamin, fragrance, preservative, surfactant, filler, sequestering agent, polymer, propellant, basifying or acidifying agent, dye, colorant, or mixture thereof.

19. The photoprotective cosmetic/dermatological composition as defined by claim 1, comprising a nonionic vesicle dispersion, emulsion, lotion, cream, milk, gel, ointment, suspension, dispersion, powder, solid stick, foam or spray.

20. The photoprotective cosmetic/dermatological composition as defined by claim 19, comprising a makeup.

21. The photoprotective cosmetic/dermatological composition as defined by claim 20, comprising an anhydrous or aqueous solid or paste, emulsion, suspension or dispersion.

22. The photoprotective cosmetic/dermatological composition as defined by claim 1, comprising a shampoo, gel, emulsion, nonionic vesicle dispersion, hair lacquer or rinse.

23. The photoprotective cosmetic/dermatological composition as defined by claim 1, comprising an oil.

24. The photoprotective cosmetic/dermatological composition as defined by claim 1, further comprising at least one additional hydrophilic or lipophilic UV-A and/or UV-B sunscreen.

25. A regimen for protecting human skin and/or hair against the deleterious effects of ultraviolet irradiation, comprising topically applying thereto an effective amount of the photoprotective cosmetic/dermatological composition as defined by claim 1.

26. A regimen for protecting human skin and/or hair against the deleterious effects of solar radiation, comprising topically applying thereto an effective amount of the photoprotective cosmetic/dermatological composition as defined by claim 1.

27. A method for stabilizing at least one dibenzoylmethane compound against the degradative effects of ultraviolet irradiation, comprising intimately admixing same with an effective photostabilizing amount of at least one polysaccharide alkyl ether wherein said at least one polysaccharide alkyl ether comprises structural units containing at least two different monosaccharide ring members, and each unit comprises at least one alkyl ether substituent.

* * * * *